United States Patent
Buchbinder et al.

(10) Patent No.: US 11,123,721 B2
(45) Date of Patent: Sep. 21, 2021

(54) TRIALKYLPHOSPHONIUM IONIC LIQUIDS, METHODS OF MAKING, AND ALKYLATION PROCESSES USING TRIALKYLPHOSPHONIUM IONIC LIQUIDS

(71) Applicant: UOP LLC, Des Plaines, IL (US)

(72) Inventors: Avram M. Buchbinder, Chicago, IL (US); Susie C. Martins, Carol Stream, IL (US); Douglas A. Nafis, Mount Prospect, IL (US); Donato Nucciarone, Stoney Creek (CA)

(73) Assignee: UOP LLC, Des Plaines, IL (US)

(*) Notice: Subject to any disclaimer, the term of this patent is extended or adjusted under 35 U.S.C. 154(b) by 52 days.

(21) Appl. No.: 16/209,738

(22) Filed: Dec. 4, 2018

(65) Prior Publication Data

US 2019/0105644 A1     Apr. 11, 2019

Related U.S. Application Data

(63) Continuation of application No. PCT/US2017/036260, filed on Jun. 7, 2017.
(Continued)

(51) Int. Cl.
*C07C 9/14*    (2006.01)
*B01J 31/02*    (2006.01)
(Continued)

(52) U.S. Cl.
CPC ....... *B01J 31/0288* (2013.01); *B01J 31/0298* (2013.01); *C07C 2/861* (2013.01);
(Continued)

(58) Field of Classification Search
None
See application file for complete search history.

(56) References Cited

U.S. PATENT DOCUMENTS

| | | |
|---|---|---|
| 4,764,440 A | 8/1988 | Jones et al. |
| 5,104,840 A | 4/1992 | Chauvin et al. |

(Continued)

FOREIGN PATENT DOCUMENTS

| | | |
|---|---|---|
| CN | 101144030 | 11/2011 |
| SU | 652186 A1 | 3/1979 |

(Continued)

OTHER PUBLICATIONS

Search Report from Corresponding PCT application No. PCT/US2017/036260, dated Oct. 12, 2017.
(Continued)

*Primary Examiner* — Yun Qian

(57) ABSTRACT

A trialkylphosphonium haloaluminate compound having a formula:

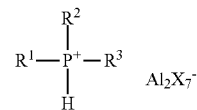

where $R^1$, $R^2$, and $R^3$ are the same or different and each is independently selected from $C_1$ to $C_8$ hydrocarbyl; and X is selected from F, Cl, Br, I, or combinations thereof is described. An ionic liquid catalyst composition incorporating the trialkylphosphonium haloaluminate compound, methods of making the trialkylphosphonium haloaluminate compound, and alkylation processes incorporating the trialkylphosphonium haloaluminate compound are also described.

12 Claims, 1 Drawing Sheet

Related U.S. Application Data

(60) Provisional application No. 62/346,813, filed on Jun. 7, 2016.

(51) Int. Cl.
*C07F 9/54* (2006.01)
*C07C 2/86* (2006.01)
*C07C 9/22* (2006.01)
C07C 7/04 (2006.01)

(52) U.S. Cl.
CPC ............... *C07C 9/14* (2013.01); *C07C 9/22* (2013.01); *C07F 9/5407* (2013.01); *B01J 2231/44* (2013.01); *C07C 7/04* (2013.01); *C07C 2531/26* (2013.01)

(56) References Cited

U.S. PATENT DOCUMENTS

| | | | |
|---|---|---|---|
| 5,824,832 | A | 10/1998 | Sherif et al. |
| 9,156,028 | B2 | 10/2015 | Martins et al. |
| 9,156,747 | B2 | 10/2015 | Martins et al. |
| 2005/0059848 | A1 | 3/2005 | Randolph et al. |
| 2012/0136189 | A1 | 5/2012 | Dötterl et al. |
| 2013/0345482 | A1 | 12/2013 | Martins et al. |
| 2013/0345483 | A1 | 12/2013 | Martins et al. |
| 2014/0213435 | A1 | 7/2014 | Martins et al. |
| 2016/0168054 | A1* | 6/2016 | Kalnes .................... B01J 31/00 585/312 |

FOREIGN PATENT DOCUMENTS

| | | |
|---|---|---|
| WO | 2014004232 A1 | 1/2014 |
| WO | 2104004232 A1 | 1/2014 |

OTHER PUBLICATIONS

Tsunashima et al., "Physicochemical properties of trialliylphosphonium-based protic ionic liquids", Electrochemistry (2012), v 80, n 11, pp. 904-906.

Matsumiya et al., "Electrochemical behaviour of hydrogen in low-viscosity phosphonium ionic liquids", Zeitschrift fur Naturforschung—Section A Journal of Physical Sciences, v 66, issue 10-11, pp. 668-674, 2011.

Cytec. "Phosphonium Salts & Ionic Liquids" https://www.cytec.com/businesses/in-process-separation/phosphine-specialties/products/phosphonium-salts-ionic-liquids (accessed Jul. 7, 2015).

Written Opinion from corresponding PCT application PCT/US2017/036260, completed on Jul. 31, 2017.

International Preliminary Report on Patentability from corresponding PCT application PCT/US2017/036260, dated Dec. 11, 2018.

International Preliminary Report on Patentability from corresponding PCT application No. PCT/US2017/036260 dated Dec. 11, 2018.

Written Opinion from corresponding PCT application No. PCT/US2017/036260 dated Oct. 12, 2017.

\* cited by examiner

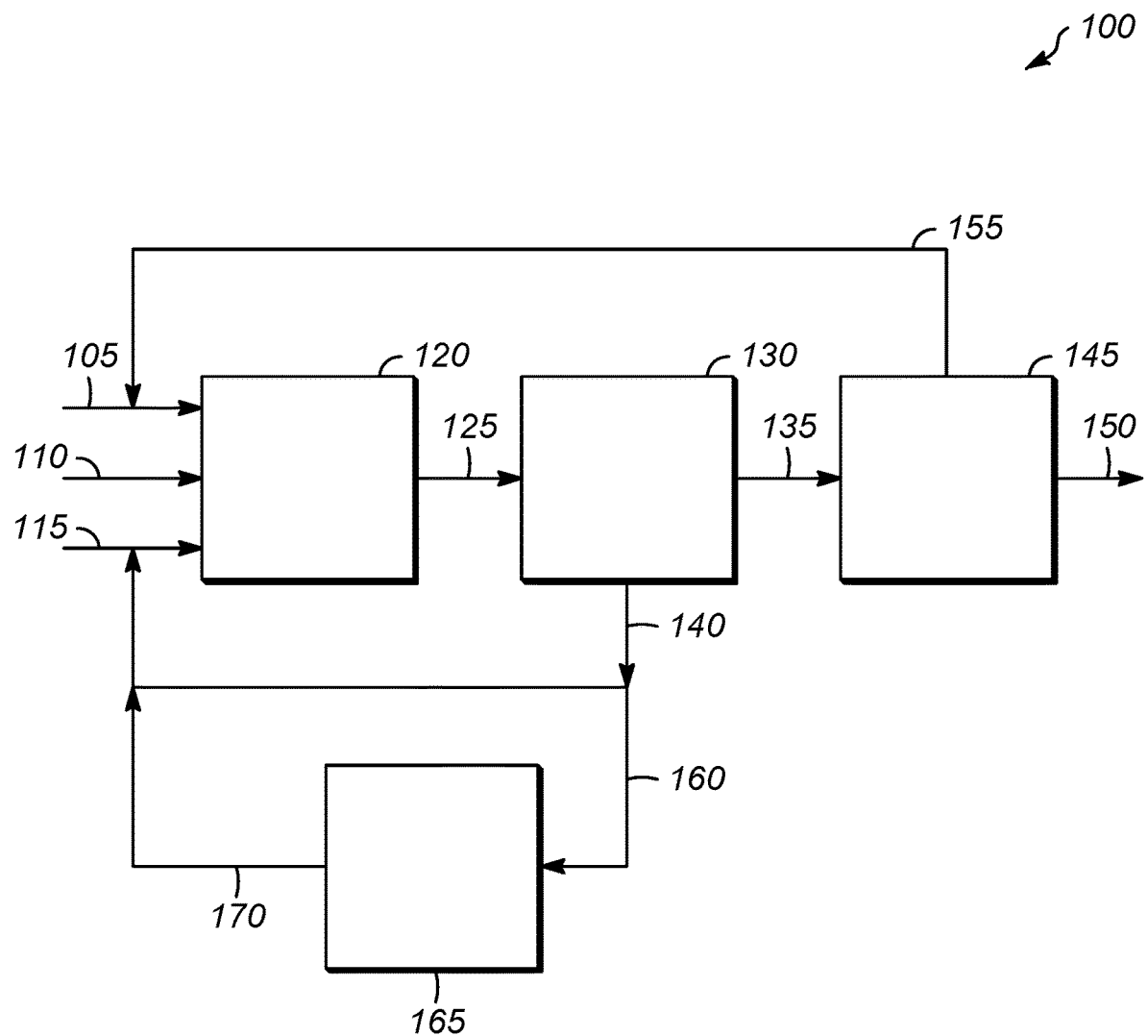

TRIALKYLPHOSPHONIUM IONIC LIQUIDS, METHODS OF MAKING, AND ALKYLATION PROCESSES USING TRIALKYLPHOSPHONIUM IONIC LIQUIDS

CROSS-REFERENCE TO RELATED APPLICATIONS

This application is a Continuation of International Application No. PCT/US2017/036260 filed Jun. 7, 2017, which application claims priority from U.S. Provisional Application No. 62/346,813 filed Jun. 7, 2016, the contents of which cited applications are hereby incorporated by reference in their entirety

BACKGROUND OF THE INVENTION

Alkylation is typically used to combine light olefins, for example mixtures of alkenes such as propylene and butylene, with isobutane to produce a relatively high-octane branched-chain paraffinic hydrocarbon fuel, including iso-heptane and isooctane. Similarly, an alkylation reaction can be performed using an aromatic compound such as benzene in place of the isobutane. When using benzene, the product resulting from the alkylation reaction is an alkylbenzene (e.g. ethylbenzene, cumene, dodecylbenzene, etc.).

The alkylation of paraffins with olefins for the production of alkylate for gasoline can use a variety of catalysts. The choice of catalyst depends on the end product a producer desires. Typical alkylation catalysts include concentrated sulfuric acid or hydrofluoric acid. However, sulfuric acid and hydrofluoric acid are hazardous and corrosive, and their use in industrial processes requires a variety of environmental controls.

Solid catalysts are also used for alkylation. Solid catalysts are more readily deactivated by the adsorption of coke precursors on the catalyst surface.

Acidic ionic liquids can be used as an alternative to the commonly used strong acid catalysts in alkylation processes. Ionic liquids are salts comprised of cations and anions which typically melt below about 100° C. Ionic liquids are essentially salts in a liquid state, and are described in U.S. Pat. Nos. 4,764,440, 5,104,840, and 5,824,832. The properties vary extensively for different ionic liquids, and the use of ionic liquids depends on the properties of a given ionic liquid. Depending on the organic cation of the ionic liquid and the anion, the ionic liquid can have very different properties.

Ionic liquids provide advantages over other catalysts, including being less corrosive than catalysts like HF, and being non-volatile.

Although ionic liquid catalysts can be very active, alkylation reactions need to be run at low temperatures, typically between −10° C. to 30° C., to maximize the alkylate quality. This requires cooling the reactor and reactor feeds, which adds substantial cost to an alkylation process utilizing ionic liquids in the form of additional equipment and energy. The most common ionic liquid catalyst precursors for alkylation include imidazolium, or pyridinium-based cations coupled with the chloroaluminate anion ($Al_2Cl_7$—).

Alkylation processes using quaternary phosphonium haloaluminate ionic liquids are known, for example, U.S. Pat. Nos. 9,156,028, and 9,156,747, and US Publication No. 2014/0213435. These patents and application cover tetraalkyl phosphonium ionic liquid catalysts of the formula:

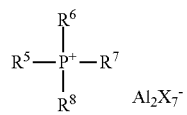

In some embodiments, $R^5$-$R^8$ comprise alkyl groups having from 4 to 12 carbon atoms, $R^5$-$R^7$ are the same alkyl group, and $R^8$ is different from $R^5$-$R^7$ and contains more carbon atoms, and X is a halogen. In other embodiments, $R^5$-$R^7$ are the same and comprise alkyl groups having from 1 to 8 carbon atoms, and $R^8$ is different from $R^5$-$R^7$ and comprises an alkyl group having from 4 to 12 carbon atoms, and X is a halogen. The quaternary phosphonium haloaluminate ionic liquids were successfully used to produce high octane products at temperatures above or near ambient. However, these ionic liquids have a viscosity in the range of 50 to 115 cSt at 25° C. This may be higher than desirable in some applications.

Therefore, there is a need for ionic liquids having a lower viscosity than quaternary phosphonium haloaluminate ionic liquids, which produce high octane alkylate, and which do not require operation under more extreme conditions such as refrigeration.

BRIEF DESCRIPTION OF THE DRAWING

The FIGURE is an illustration of one embodiment of an alkylation process of the present invention.

SUMMARY OF THE INVENTION

One aspect of the invention is a trialkylphosphonium haloaluminate compound. In one embodiment, the trialkylphosphonium haloaluminate compound has the formula:

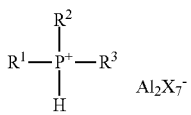

where $R^1$, $R^2$, and $R^3$ are the same or different and each is independently selected from $C_1$ to $C_8$ hydrocarbyl; and X is selected from F, Cl, Br, I, or combinations thereof; with the proviso that when X is Cl, $R^1$, $R^2$, and $R^3$ are not all methyl.

Another aspect of the invention is an ionic liquid catalyst composition. In one embodiment, the ionic liquid catalyst composition comprises one or more trialkylphosphonium haloaluminate compounds as described above.

Another aspect of the invention is a process of making the trialkylphosphonium haloaluminate compound. In one embodiment, the process includes reacting a trialkylphosphonium halide having a general formula:

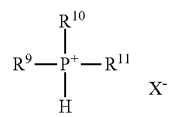

where $R^9$ $R^{10}$, and $R^{11}$ are the same or different and each is independently selected from $C_1$ to $C_8$ hydrocarbyl; and X is selected from F, Cl, Br, or I; with at least one of $AlCl_3$, $AlBr_3$ or $AlI_3$ to form the trialkylphosphonium haloaluminate ionic liquid compound.

Another aspect of the invention is an alkylation process. In one embodiment, the alkylation process includes contacting an isoparaffin feed having from 4 to 10 carbon atoms and an olefin feed having from 2 to 10 carbon atoms in the presence of a trialkylphosphonium ionic liquid catalyst composition in an alkylation zone under alkylation conditions to generate an alkylate. The trialkylphosphonium ionic liquid catalyst composition comprises one or more trialkylphosphonium haloaluminate compounds having a formula:

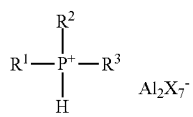

where $R^1$, $R^2$, and $R^3$ are the same or different and each is independently selected from $C_1$ to $C_8$ hydrocarbyl; and X is selected from F, Cl, Br, I, or combinations thereof.

DETAILED DESCRIPTION OF THE INVENTION

The present invention relates to trialkylphosphonium haloaluminate compounds, ionic liquid catalysts compositions comprising trialkylphosphonium haloaluminate compositions, processes of making the trialkylphosphonium haloaluminate compounds, and alkylation processes using the ionic liquid catalyst compositions.

The trialkylphosphonium haloaluminate compounds have the formula:

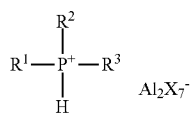

where $R^1$, $R^2$, and $R^3$ are the same or different and each is independently selected from $C_1$ to $C_8$ hydrocarbyl; and X is selected from F, Cl, Br, I, or combinations thereof.

In some embodiments, $R^1$, $R^2$, and $R^3$ are selected from $C_1$ to $C_6$ hydrocarbyl, or $C_3$ to $C_6$ hydrocarbyl, or $C_3$ to $C_5$ hydrocarbyl. In some embodiments, $R^1$, $R^2$, and $R^3$ have the same number of carbon atoms. In some embodiments, $R^1$, $R^2$, and $R^3$ are identical. In some embodiments, $R^1$, $R^2$, and $R^3$ are selected from the group consisting of methyl, ethyl, propyl, butyl, pentyl, and hexyl (including all isomers, e.g., butyl may be n-butyl, sec-butyl, isobutyl, and the like).

In some embodiments, when X is Cl, $R^1$, $R^2$, and $R^3$ are not all methyl. In some embodiments, when X is Cl, only one of $R^1$, $R^2$, and $R^3$ is methyl. In some embodiments, when X is Cl, $R^1$, $R^2$, and $R^3$ are not methyl.

The term "hydrocarbyl" as used herein is used in its ordinary sense and is meant to encompass aliphatic (linear or branched), alicyclic, and aromatic groups having an all-carbon backbone and consisting of carbon and hydrogen atoms, typically from 1 to 36 carbon atoms in length. Examples of hydrocarbyl groups include alkyl, cycloalkyl, cycloalkenyl, carbocyclic aryl, alkenyl, alkynyl, alkylcycloalkyl, cycloalkylalkyl, cycloalkenylalkyl, and carbocyclic aralkyl, alkaryl, aralkenyl and aralkynyl groups. Those skilled in the art will appreciate that while preferred embodiments are discussed in more detail below, multiple embodiments of the phosphonium haloaluminate compounds as defined above are contemplated as being within the scope of the present invention.

In some embodiments, the trialkylphosphonium haloaluminate compound is tri-n-butylphosphonium $Al_2Cl_7—$. In some embodiments, the trialkylphosphonium haloaluminate compound is tri-isobutylphosphonium $Al_2Cl_7—$. In some embodiments, the trialkylphosphonium haloaluminate compound is di-n-butyl-sec-butylphosphonium $Al_2Cl_7—$.

In some embodiments, the trialkylphosphonium haloaluminate compound has the formula

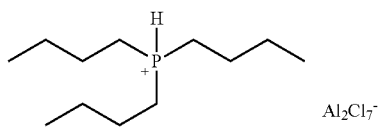

Another aspect of the invention is an ionic liquid catalyst composition. The ionic liquid catalyst composition can comprise one or more trialkylphosphonium haloaluminate compounds, as described above.

In some embodiments, the initial kinematic viscosity of the ionic liquid catalyst composition is less than about 70 cSt at 25° C., or less than about 65 cSt, or less than about 60 cSt, or less than about 55 cSt, or less than about 50 cSt, or less than about 45 cSt, or less than about 40 cSt. In some embodiments, the initial kinematic viscosity of the ionic liquid catalyst is less than about 45 cSt at 38° C., or less than about 40 cSt, or less than about 35 cSt, or less than about 30 cSt, or less than about 25 cSt. In some embodiments, the initial kinematic viscosity of the ionic liquid catalyst is less than about 33 cSt at 50° C., or less than about 30 cSt, or less than about 25 cSt, or less than about 20 cSt, or less than about 18 cSt.

The relative density of the ionic liquid is typically in the range of about 1.10 to about 1.35 g/cm$^3$ at 25° C. using ASTM method D4052 for chloroaluminates, or about 1.20 to about 1.25 g/cm$^3$.

In some embodiments, the molar ratio of aluminum to phosphorous in the ionic liquid catalyst composition is in the range of 1.8 to 2.2.

The ionic liquid catalyst composition can include other ionic liquids. In some embodiments, the ionic liquid catalyst composition can include a quaternary phosphonium haloaluminate compound having a formula:

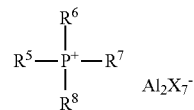

where $R^5$-$R^7$ are the same or different and each is independently selected from a $C_1$ to $C_8$ hydrocarbyl; $R^8$ is different from $R^5$-$R^7$ and is selected from a $C_1$ to $C_{15}$ hydrocarbyl; and X is selected from F, Cl, Br, I, or combinations thereof. In some embodiments, each of $R^5$-$R^7$ is independently chosen from a $C_3$-$C_6$ alkyl. In some embodiments, $R^5$-$R^7$ are the same. In some embodiments, $R^8$ is a $C_4$-$C_{12}$ hydrocarbyl. In some embodiments, $R^8$ is a $C_4$-$C_8$ alkyl.

The concentration of the one or more trialkylphosphonium haloaluminate compounds is about 5 mol % to about 100 mol % of the total concentration of the ionic liquid compounds, or about 10 mol % to about 100 mol %, about 15 mol % to about 100 mol %, or about 20 mol % to about 100 mol %, or about 25 mol % to about 100 mol %, or about 30 mol % to about 100 mol %, or about 35 mol % to about 100 mol %, or about 40 mol % to about 100 mol %, or about 45 mol % to about 100 mol %, or about 50 mol % to about 100 mol %, or about 55 mol % to about 100 mol %, or about 60 mol % to about 100 mol %, or about 65 mol % to about 100 mol %, or about 70 mol % to about 100 mol %, or about 75 mol % to about 100 mol %, or about 80 mol % to about 100 mol %, or about 85 mol % to about 100 mol %, or about 90 mol % to about 100 mol %. The co-catalyst is not included in the mol % of the ionic liquid compounds. In some embodiments, there may be less than about 1 mol % impurities.

In embodiments containing one or more quaternary phosphonium haloaluminate compounds, the concentration of the one or more trialkylphosphonium haloaluminate compounds is about 5 mol % to about 98 mol % of the total concentration of the ionic liquid compounds, or about 10 mol % to about 98 mol %, about 15 mol % to about 98 mol %, or about 20 mol % to about 98 mol %, or about 25 mol % to about 98 mol %, or about 30 mol % to about 98 mol %, or about 35 mol % to about 98 mol %, or about 40 mol % to about 98 mol %, or about 45 mol % to about 98 mol %, or about 50 mol % to about 98 mol %, or about 55 mol % to about 98 mol %, or about 60 mol % to about 98 mol %, or about 65 mol % to about 98 mol %, or about 70 mol % to about 98 mol %, or about 75 mol % to about 98 mol %, or about 80 mol % to about 98 mol %, or about 85 mol % to about 98 mol %, or about 90 mol % to about 98 mol %. The concentration of the one or more tetraalkylphosphonium haloaluminate compounds is about 2 mol % to about 95 mol % of the total concentration of the ionic liquid compounds, or about 2 mol % to about 90 mol %, or about 2 mol % to about 85 mol %, or about 2 mol % to about 80 mol %, or about 2 mol % to about 75 mol %, or about 2 mol % to about 70 mol %, or about 2 mol % to about 65 mol %, or about 2 mol % to about 60 mol %, or about 2 mol % to about 55 mol %, or about 2 mol % to about 50 mol %, or about 2 mol % to about 45 mol %, or about 2 mol % to about 40 mol %, or about 2 mol % to about 35 mol %, or about 2 mol % to about 30 mol %, or about 2 mol % to about 25 mol %, or about 2 mol % to about 20 mol %, or about 2 mol % to about 15 mol %, or about 2 mol % to about 10 mol %. The co-catalyst is not included in the mol % of the ionic liquid compounds.

In some embodiments, the trialkylphosphonium haloaluminate compound is present at a concentration from about 51 mol % to about 98 mol % of the total concentration of the ionic liquid catalyst composition.

In some embodiments, the ionic liquid catalyst composition can include a co-catalyst (or catalyst promoter). The co-catalyst is present in an amount of about 0.05 mol to about 1 mol of co-catalyst per mol of haloaluminate ionic liquid, or about 0.05 mol to about 0.7 mol, or about 0.06 mol to about 0.5 mol, or about 0.15 mol to about 0.7 mol, or about 0.15 mol to about 0.5 mol. The co-catalyst may be a Brønsted acid and/or a Brønsted acid precursor. Suitable Brønsted acid include, but are not limited to, HCl, HBr, HI, and mixtures thereof. Suitable Brønsted acid precursors include, but are not limited to, 2-chlorobutane, 2-chloro-2-methylpropane, 1-chloro-2-methylpropane, 1-chlorobutane, 2-chloropropane, 1-chloropropane and other chloroalkanes, preferably secondary or tertiary chloroalkanes, or combinations thereof.

The trialkylphosphonium haloaluminate ionic liquid compound can be made by reacting a trialkylphosphonium halide having a general formula:

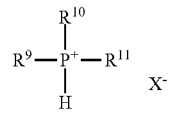

with at least one of $AlCl_3$, $AlBr_3$ or $AlI_3$ to form the trialkylphosphonium haloaluminate ionic liquid compound. $R^9$, $R^{10}$, and $R^{11}$ are the same or different and each is independently selected from $C_1$ to $C_8$ hydrocarbyl; and X is selected from F, Cl, Br, or I.

In some embodiments, $R^9$, $R^{10}$, and $R^{11}$ are selected from $C_1$ to $C_6$ hydrocarbyl, or $C_3$ to $C_6$ hydrocarbyl, or $C_3$ to $C_5$ hydrocarbyl, or $C_4$ hydrocarbyl. In some embodiments, $R^9$, $R^{10}$, and $R^{11}$ have the same number of carbon atoms. In some embodiments, $R^9$, $R^{10}$, and $R^{11}$ identical. In some embodiments, $R^9$, $R^{10}$, and $R^{11}$ are selected from the group consisting of methyl, ethyl, propyl, butyl, pentyl, and hexyl (including all isomers, e.g., butyl may be n-butyl, sec-butyl, isobutyl, and the like).

In some embodiments, the trialkylphosphonium halide comprises trimethyl phosphonium halide, triethyl phosphonium halide, tripropyl phosphonium halide, tri n-butyl phosphonium halide, tri-isobutyl phosphonium halide, di-n-butyl-sec-butylphosphonium halide, tripentyl phosphonium halide, trihexylphosphonium halide, or combinations thereof. The reaction can take place at a temperature in the range of about 20° C. to about 170° C. and under an inert environment.

The reaction can utilize about 1.8 to about 2.2 molar equivalents of $AlCl_3$, $AlBr_3$ or $AlI_3$.

The ionic liquid catalyst composition can be used in alkylation reactions. It has been found that alkylation reactions using trialkylphosphonium haloaluminate ionic liquids give high octane products when carried out at temperatures above or near ambient temperature. This provides for an operation that can substantially save on cost by removing refrigeration equipment from the process. The present invention provides a process for the alkylation of paraffins using trialkylphosphonium haloaluminate ionic liquids.

The acidity of the ionic liquid catalyst composition needs to be controlled to provide for suitable alkylation conditions. Brønsted acids and Brønsted acid precursors may be employed as a co-catalyst to enhance the activity of the catalyst composition by boosting the overall acidity of the trialkylphosphonium ionic liquid catalyst composition. Suitable Brønsted acids and Brønsted acid precursors are discussed above.

Typical alkylation reaction conditions include a temperature in the range of about −20° C. to the decomposition temperature of the ionic liquid, or about −20° C. to about 100° C., or about −20° C. to about 80° C., or about 0° C. to about 80° C., or about 20° C. to about 80° C., or about 20° C. to about 70° C., or about 20° C. to about 50° C. Ionic liquids can also solidify at moderately high temperatures, and therefore it is preferred to have an ionic liquid that maintains its liquid state through a reasonable temperature span. In some embodiments, cooling may be needed. If cooling is needed, it can be provided using any known methods.

The pressure is typically in the range of atmospheric (0.1 MPa(g)) to about 8.0 MPa(g), or about 0.3 MPa(g) to about 2.5 MPa(g). The pressure is preferably sufficient to keep the reactants in the liquid phase.

The residence time of the reactants in the reaction zone is in the range of a few seconds to hours, or about 0.5 min to about 60 min, or about 1 min to about 60 min, or about 3 min to about 60 min.

The ionic liquid catalyst composition volume in the reactor may be from about 1 vol % to about 75 vol % of the total volume of material in the reactor (ionic liquid catalyst composition and hydrocarbons), or about 1 vol % to about 70 vol %, or about 1 vol % to about 65 vol %, or about 1 vol % to about 60 vol %, or about 1 vol % to about 55 vol %, or about 1 vol % to about 50 vol %, or about 1 vol % to about 45 vol %, or about 1 vol % to about 40 vol %, or about 1 vol % to about 35 vol %, or about 1 vol % to about 30 vol %, or about 1 vol % to about 25 vol %, or about 1 vol % to about 20 vol %, or about 1 vol % to about 15 vol %, or about 1 vol % to about 10 vol %, or about 1 vol % to about 5 vol %.

Due to the low solubility of hydrocarbons in ionic liquids, olefins-isoparaffins alkylation, like most reactions in ionic liquids, is generally biphasic and takes place at the interface in the liquid state. The catalytic alkylation reaction is generally carried out in a liquid hydrocarbon phase, in a batch system, a semi-batch system or a continuous system using one reaction stage as is usual for aliphatic alkylation. The isoparaffin and olefin can be introduced separately or as a mixture. The molar ratio between the isoparaffin and the olefin is in the range of about 1:1 to about 100:1, for example, or in the range of about 2:1 to about 50:1, or about 2:1 to about 40:1, or about 2:1 to about 30:1, or about 2:1 to about 20:1, or about 2:1 to about 15:1, or about 5:1 to about 50:1, or about 5:1 to about 40:1, or about 5:1 to about 30:1, or about 5:1 to about 20:1, or about 5:1 to about 15:1, or about 8:1 to about 50:1, or about 8:1 to about 40:1, or about 8:1 to about 30:1, or about 8:1 to about 20:1, or about 8:1 to about 15:1.

In a semi-batch system, the ionic liquid catalyst composition (including the trialkylphosphonium haloaluminate compound(s), optional co-catalyst, and any quaternary phosphonium haloaluminate compound(s)) and isoparaffin are introduced first, followed by the olefin or a mixture of isoparaffin and olefin. The catalyst is measured in the reactor with respect to the amount of olefins, with a catalyst to olefin weight ratio between about 0.1 and about 10, or between about 0.2 and about 5, or between about 0.5 and about 2. Vigorous stirring is desirable to ensure good contact between the reactants and the catalyst. The reaction temperature can be in the range of about 0° C. to about 100° C., or about 20° C. to about 70° C. The pressure can be in the range from atmospheric pressure to about 8000 kPa, preferably sufficient to keep the reactants in the liquid phase. Residence time of reactants in the vessel is in the range of a few seconds to hours, preferably about 0.5 min to about 60 min. The heat generated by the reaction can be eliminated using any of the means known to the skilled person. At the reactor outlet, the hydrocarbon phase is separated from the ionic liquid phase by gravity settling based on density differences, or by other separation techniques known to those skilled in the art. Then the hydrocarbons are separated by distillation and the starting isoparaffin which has not been converted is recycled to the reactor.

In a continuous system, the ionic liquid catalyst composition (including the trialkylphosphonium haloaluminate compound(s), optional co-catalyst, and any quaternary phosphonium haloaluminate compound(s)), the isoparaffin, and the olefin are each added continuously. The ionic liquid catalyst composition, unreacted isoparaffin, and unreacted olefin are each removed continuously from the reaction zone along with alkylate product. The ionic liquid catalyst composition, unreacted isoparaffin, and/or unreacted olefin may be recycled. The olefin may be added to one or more locations in the reaction zone. It is preferable to add the olefin to multiple locations in the reaction zone. Adding olefin in multiple locations, or spreading the olefin addition over a longer period of time results in a higher isoparaffin to olefin ratio measured in a specific location at a specific point in time. The isoparaffin to olefin ratio is defined as the cumulative amount of isoparaffin divided by the cumulative amount of olefin added across the entire reaction zone.

Typical alkylation conditions may include an ionic liquid catalyst composition volume in the reactor of from about 1 vol % to about 50 vol %, a temperature of from about 0° C. to about 100° C., a pressure of from about 300 kPa to about 2500 kPa, an isobutane to olefin molar ratio of from about 2:1 to about 20:1, and a residence time of about 5 min to about 1 hour. The paraffin used in the alkylation process preferably comprises an isoparaffin having from 4 to 10 carbon atoms, or 4 to 8 carbon atoms, or 4 to 5 carbon atoms. The olefin used in the alkylation process preferably has from 2 to 10 carbon atoms, or 3 to 8 carbon atoms, or 3 to 5 carbon atoms.

One application of the alkylation process is to upgrade low value $C_4$ hydrocarbons to higher value alkylates. To that extent, one specific embodiment is the alkylation of butanes with butylenes to generate $C_8$ compounds. Preferred products include trimethylpentanes (TMP), and while other $C_8$ isomers are produced, the prevalent competing isomers are dimethylhexanes (DMH). The quality of the product stream can be measured in the ratio of TMP to DMH, with a high ratio desired.

In another embodiment, the invention comprises passing an isoparaffin and an olefin to an alkylation reactor, where the alkylation reactor includes an ionic liquid catalyst to react the olefin with the isoparaffin to generate an alkylate. The isoparaffin has from 4 to 10 carbon atoms, and the olefin has from 2 to 10 carbon atoms. The ionic liquid catalyst composition comprises the trialkylphosphonium haloaluminates described above.

The FIGURE illustrates one embodiment of an alkylation process 100 utilizing the trialkylphosphonium ionic liquid catalyst composition. An isoparaffin feed stream 105, an olefin feed stream 110, and a trialkylphosphonium ionic liquid catalyst composition stream 115 (including the trialkylphosphonium haloaluminate compound(s), optional co-catalyst, and any quaternary phosphonium haloaluminate compound(s)) are fed to an alkylation zone 120. The isoparaffin and the olefin react in the presence of the trialkylphosphonium ionic liquid catalyst composition to form alkylate.

The effluent 125 from the alkylation zone 120 contains alkylate, unreacted isoparaffins, the trialkylphosphonium ionic liquid catalyst composition, and possibly unreacted olefins. The effluent 125 is sent to a separation zone 130 where it is separated into a hydrocarbon stream 135 comprising the alkylate and unreacted isoparaffins (and any unreacted olefins) and an ionic liquid recycle stream 140 comprising the trialkylphosphonium ionic liquid catalyst composition. Suitable separation zones include, but are not limited to, gravity settlers, coalescers, filtration zones comprising sand or carbon, adsorption zones, scrubbing zones, or combinations thereof.

The hydrocarbon stream 135 is sent to a hydrocarbon separation zone 145 where it is separated into an alkylate stream 150 and an isoparaffin recycle stream 155. The alkylate stream 150 can be recovered and further treated as needed. The isoparaffin recycle stream 155 can be recycled to the alkylation zone 120, if desired. Suitable hydrocarbon separation zones include, but are not limited to, distillation or vaporization.

The ionic liquid recycle stream 140 can be recycled to the alkylation zone 120, if desired. In some embodiments, at least a portion 160 of the ionic liquid recycle stream 140 can be sent to a regeneration zone 165 to regenerate the trialkylphosphonium ionic liquid catalyst composition. The regenerated ionic liquid recycle stream 170 can be recycled to the alkylation zone.

Various methods for regenerating ionic liquids could be used. For example, U.S. Pat. Nos. 7,651,970; 7,825,055; 7,956,002; 7,732,363, each of which is incorporated herein by reference, describe contacting ionic liquid containing the conjunct polymer with a reducing metal (e.g., Al), an inert hydrocarbon (e.g., hexane), and hydrogen and heating to about 100° C. to transfer the conjunct polymer to the hydrocarbon phase, allowing for the conjunct polymer to be removed from the ionic liquid phase. Another method involves contacting ionic liquid containing conjunct polymer with a reducing metal (e.g., Al) in the presence of an inert hydrocarbon (e.g. hexane) and heating to about 100° C. to transfer the conjunct polymer to the hydrocarbon phase, allowing for the conjunct polymer to be removed from the ionic liquid phase. See e.g., U.S. Pat. No. 7,674,739 B2; which is incorporated herein by reference. Still another method of regenerating the ionic liquid involves contacting the ionic liquid containing the conjunct polymer with a reducing metal (e.g., Al), HCl, and an inert hydrocarbon (e.g. hexane), and heating to about 100° C. to transfer the conjunct polymer to the hydrocarbon phase. See e.g., U.S. Pat. No. 7,727,925, which is incorporated herein by reference. The ionic liquid can be regenerated by adding a homogeneous metal hydrogenation catalyst (e.g., (PPh$_3$)$_3$RhCl) to ionic liquid containing conjunct polymer and an inert hydrocarbon (e.g. hexane), and introducing hydrogen. The conjunct polymer is reduced and transferred to the hydrocarbon layer. See e.g., U.S. Pat. No. 7,678,727, which is incorporated herein by reference. Another method for regenerating the ionic liquid involves adding HCl, isobutane, and an inert hydrocarbon to the ionic liquid containing the conjunct polymer and heating to about 100° C. The conjunct polymer reacts to form an uncharged complex, which transfers to the hydrocarbon phase. See e.g., U.S. Pat. No. 7,674,740, which is incorporated herein by reference. The ionic liquid could also be regenerated by adding a supported metal hydrogenation catalyst (e.g. Pd/C) to the ionic liquid containing the conjunct polymer and an inert hydrocarbon (e.g. hexane). Hydrogen is introduced and the conjunct polymer is reduced and transferred to the hydrocarbon layer. See e.g., U.S. Pat. No. 7,691,771, which is incorporated herein by reference. Still another method involves adding a suitable substrate (e.g. pyridine) to the ionic liquid containing the conjunct polymer. After a period of time, an inert hydrocarbon is added to wash away the liberated conjunct polymer. The ionic liquid precursor [butylpyridinium][Cl] is added to the ionic liquid (e.g. [butylpyridinium][Al$_2$Cl$_7$]) containing the conjunct polymer followed by an inert hydrocarbon. After mixing, the hydrocarbon layer is separated, resulting in a regenerated ionic liquid. See, e.g., U.S. Pat. No. 7,737,067, which is incorporated herein by reference. Another method involves adding ionic liquid containing conjunct polymer to a suitable substrate (e.g. pyridine) and an electrochemical cell containing two aluminum electrodes and an inert hydrocarbon. A voltage is applied, and the current measured to determine the extent of reduction. After a given time, the inert hydrocarbon is separated, resulting in a regenerated ionic liquid. See, e.g., U.S. Pat. No. 8,524,623, which is incorporated herein by reference. Ionic liquids can also be regenerated by contacting with silane compounds (U.S. Pat. No. 9,120,092), borane compounds (U.S. Publication No. 2015/0314281), Brønsted acids, (U.S. Pat. No. 9,079,176), or C$_1$ to C$_{10}$ paraffins (U.S. Pat. No. 9,079,175), each of which is incorporated herein by reference. Regeneration processes utilizing silane and borane compounds are described in U.S. application Ser. Nos. 14/269,943 and 14/269,978, each of which is incorporated herein by references.

EXAMPLES

Example 1

Synthesis of Tributylphosphonium Heptachlorodialuminate (TBP-Al$_2$Cl$_7$)

The synthetic route for tributylphosphonium heptachlorodialuminate is depicted below and described in detail:

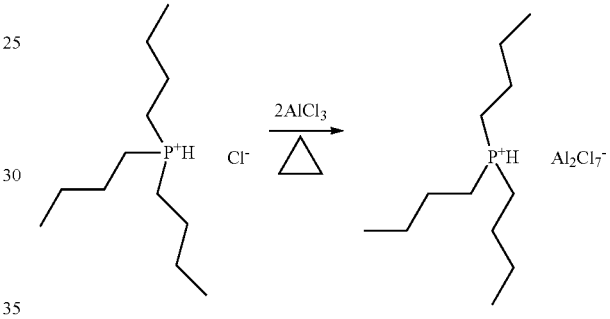

A) Tributylphosphonium chloride (70.3 g, 0.294 moles) is added to a 500 mL round bottom flask equipped with a stir bar, thermowell, a screw-type solids addition funnel and nitrogen supply valve under a nitrogen atmosphere. The flask is initially warmed to 50° C., then up to 120° C. (to maintain a molten mixture) while adding granular aluminum chloride (77.9 g, 0.584 moles (as AlCl$_3$)). After complete addition of the aluminum chloride, the reaction mixture is allowed to stir for an additional two hours, then cooled with agitation for another hour. The liquid product is isolated and stored under nitrogen. A total of 139 g of trialkylphosphonium heptachlorodialuminate is recovered analyzing as 97% tri(n-butyl)phosphonium heptachlorodialuminate and 3% di(n-butyl)(s-butyl)phosphonium heptachlorodialuminate ($^{31}$P NMR area percent) (synthesized by Cytec Canada Inc., of Welland, Ontario). ($^{31}$P NMR area percent). $^{31}${$^1$H} NMR (243 MHz, CD$_3$CN): δ20.55 (singlet, PH(CH$_2$CH$_2$CH$_2$CH$_3$)$_2$(CH(CH$_3$)CH$_2$CH$_3$), minor), δ12.70 (singlet, PH(CH$_2$CH$_2$CH$_2$CH$_3$)$_3$, major). $^1$H NMR (600 MHz, CD$_3$CN): δ5.92 (dp, $^1J_{HP}$=476 Hz, $^3J_{HH}$=5.4 Hz, 0.34 H, PH(CH$_2$CH$_2$CH$_2$CH$_3$)$_3$), δ2.196 (m, 2.02 H, PH(CH$_2$CH$_2$CH$_2$CH$_3$)$_3$), δ1.605 (m, 2.03 H, PH(CH$_2$CH$_2$CH$_2$CH$_3$)$_3$), δ1.477 (sextet, $^3J_{HH}$=7.2 Hz, 2.04 H, PH(CH$_2$CH$_2$CH$_2$CH$_3$)$_3$), δ0.963 (t, $^3J_{HH}$=7.8 Hz, 3.00 H, PH(CH$_2$CH$_2$CH$_2$CH$_3$). $^{13}$C {$^1$H} NMR (151 MHz, CD$_3$CN): δ24.215 (d, J$_{CP}$=4.53 Hz), δ23.31 (d, J$_{CP}$=15.1 Hz), δ16.10 (d, J$_{CP}$=45 Hz), δ12.76 (s).

B) Reagents are weighed in the glove box. 132.26 g (0.5539 mol) of Bu$_3$PHCl is placed into a 500 mL flask and 147.74 g (1.1080 mol) of AlCl$_3$ is added via a solid addition funnel. Under N$_2$ purging, the glassware is assembled in the fume hood along with a water-cooled condenser and magnetic stir bar. The Bu₃PHCl is heated to about 60° C., and the heat turned off to start the addition, which is exothermic. The AlCl₃ is added at a rate to maintain an internal temperature of about 100° C. The mixture of the two reagents at about half way through the addition solidifies at about 94° C. The addition is stopped, and heat is applied to 100° C. The addition is started again. The reaction pot is solidifying even at 107° C. The addition is stopped and continued the following day. On cooling, the pot contents fully solidified, and the heat is set to 100° C. The lower half of the flask becomes molten while the upper stays solid. A heat gun is used to gently heat the edges and melt the upper portion. The thermowell tip still has material solidified around it, and when it releases the temperature increases rapidly to 124-125° C. The heat is turned off, and the pot is left to cool closer to 100° C. Around 108° C., the pot contents start going solid again, the heat is then set to 120° C. When the pot contents are homogeneous and stirring efficiently, the addition of AlCl₃ is continued. Gas formation ceases shortly within the exothermic activity subsiding on addition. Once all solids are added, the pot is left to stir set at 100° C. for 30 minutes. As there are still solids floating in the mix and some crusting around the flask necks, the flask was shaken to try to rinse the residue into the pot. The flask is stirred for an additional 40 minutes at 100° C. then removed. The material is transferred to jars in the glove box. A 30 mL jar is removed from the glove box and opened under N₂ to sample for NMR. A total of 271.4 g of trialkylphosphonium heptachlorodialuminate is recovered analyzing as 97% tri (n-butyl)phosphonium heptachlorodialuminate and 3% di(n-butyl)(s-butyl)phosphonium heptachlorodialuminate ($^{31}$P NMR area percent) (synthesized by Cytec Canada Inc., of Welland, Ontario).

Alkylation Experiments

Comparative Example 1

7.999 g (0.0139 mol) of tributylpentylphosphonium (TBPP) heptachlorodialuminate ionic liquid, prepared by a method analogous to the method described in Example 1 of US Publication No. 2013/0345484, was loaded in a 300 cc autoclave with 0.422 g (0.0046 mol) of 2-chlorobutane (used as a co-catalyst). The autoclave was fitted with a Cowles-type impeller. 80 g of isobutane was charged, and the reactor was pressurized to about 3.4 MPa(g) (500 psig) with nitrogen. After pressurizing the reactor, the mixture was stirred at 1700-1900 rpm for 20 minutes to ensure breakdown of the 2-chlorobutane. The reaction was initiated by the addition of approximately 8 g of 2-butenes (mixed cis- and trans-isomers) over the course of 2.5 minutes while mixing at 1900 rpm. The 2-butenes blend also contained about 8.5 wt % n-pentane that was used as a tracer to verify the amount of butenes added (butenes added=wt % n-pentane added*wt % butenes in feed/wt % n-pentane in feed). Mixing was stopped, and the mixture was allowed to settle. The hydrocarbon was analyzed by gas chromatography (GC). Table 2 shows the results. The n-pentane tracer indicated that 7.95 g of 2-butenes were added. The butenes conversion was 99.94%. The hydrocarbon contained 19.5 wt % $C_{5+}$ (products having 5 carbon atoms or more). Of the $C_{5+}$ products, 72.3% was octanes, 6.8% was isopentane, 5.8% was hexanes, 5.1% was heptanes, and 10.1% was $C_{9+}$ (products containing 9 carbon atoms or more). Among the octanes, the ratio of trimethylpentanes to dimethylhexanes (TMP/DMH) was 12.6. The calculated research octane number (RONC) was 95.1. The results are shown in Table 2.

The selectivity to a particular product or group of products is defined as the amount of the particular product or group of products in weight percent, divided by the amount of products containing a number of carbon atoms greater than the number of carbon atoms in one isoparaffin reactant in weight percent. For example for the alkylation of isobutane and butene, the selectivity for $C_8$ hydrocarbons is the wt % of hydrocarbons containing exactly 8 carbon atoms in the product divided by the wt % of all products containing 5 or more carbon atoms. Similarly, the selectivity to $C_5$-$C_7$ hydrocarbons is the wt % of hydrocarbons containing exactly 5, 6 or 7 carbon atoms in the product divided by the wt % of all products containing 5 or more carbon atoms, and the selectivity to $C_{9+}$ hydrocarbons is the wt % of hydrocarbons containing 9 or more carbon atoms in the product divided by the wt % of all products containing 5 or more carbon atoms.

Research octane number, calculated (RONC) is determined by summing the volume normalized blending octanes of all products i containing 5 carbons or more according to:

$$RONC = \frac{1}{V}\sum_i BN_i \frac{m_i}{\rho_i}$$

where BN are blending octane numbers shown in Table 1, $m_i$ is the mass of product i in the stream, $\rho_i$ is the pure component density of product i, and V is the total volume of all products (not including un-reacted feeds, or ionic liquid).

TABLE 1

Density and Octane Blending Numbers for Alkylation Products

| Compound Name | Density g/cc | BN |
|---|---|---|
| Ethane | 0.409661 | 0 |
| Propane | 0.507652 | 0 |
| n-butane | 0.584344 | 95 |
| isopentane | 0.6247 | 93.5 |
| 2,2-dimethylbutane | 0.653938 | 94 |
| 2,3-dimethylbutane | 0.6664 | 103 |
| 2-methylpentane | 0.6579 | 74 |
| 3-methylpentane | 0.6689 | 75.5 |
| n-hexane | 0.6640 | 31.0 |
| 2,2,3-trimethylbutane | 0.6901 | 112.1 |
| 2,2-dimethylpentane | 0.6782 | 92.8 |
| 2,3-dimethylpentane | 0.6996 | 91 |
| 2,4-dimethylpentane | 0.6773 | 83 |
| 3,3-dimethylpentane | 0.6976 | 80.8 |
| 2-methylhexane | 0.683 | 42.4 |
| 3-methylhexane | 0.6917 | 52 |
| 2,2,3-trimethylpentane | 0.7202 | 109 |
| 2,2,4-trimethylpentane | 0.6962 | 100 |
| 2,3,3-trimethylpentane | 0.7303 | 106 |
| 2,3,4-trimethylpentane | 0.7233 | 102.5 |
| 2,2-dimethylhexane | 0.6997 | 72.5 |
| 2,3-dimethylhexane | 0.7165 | 56 |
| 2,4-dimethylhexane | 0.7013 | 60 |
| 2,5-dimethylhexane | 0.6979 | 55 |
| 3,3-dimethylhexane | 0.7143 | 75.5 |
| 2-methylheptane | 0.7021 | 25 |
| 3-methylheptane | 0.7101 | 25 |
| 4-methylheptane | 0.7000 | 24.0 |
| Lumped C9+ | 0.74 | 78.5 |

Example 2

7.005 g (0.0139 mol) of tributylphosphonium (TBP) heptachlorodialuminate ionic liquid from example 1A was loaded in a 300 cc autoclave with 0.335 g (0.0036 mol) of 2-chlorobutane. The autoclave was fitted with a Cowles-type impeller. 80 g of isobutane was charged, and the reactor was pressurized to about 3.4 MPa(g) (500 psig) with nitrogen. After pressurizing the reactor, the mixture was stirred at 1700-1900 rpm for 20 minutes to ensure breakdown of the 2-chlorobutane. The reaction was initiated by the addition of approximately 8 g of 2-butenes (mixed cis- and trans-isomers) over the course of 2.5 minutes while mixing at 1900 rpm. The 2-butenes blend also contained about 8.5 wt % n-pentane that was used as a tracer to verify the amount of butenes added. The mixing was stopped, and the mixture was allowed to settle. The hydrocarbon was analyzed by gas chromatography (GC). Table 2 shows the results. The n-pentane tracer indicated that 7.98 g of 2-butenes were added. The butenes conversion was 99.95%. The hydrocarbon contained 19.6 wt % $C_{5+}$. Of the $C_{5+}$ products, 72.4% was octanes, 8.6% was isopentane, 5.7% was hexanes, 4.6% was heptanes and 8.7% was $C_{9+}$. Among the octanes, the ratio of trimethylpentanes to dimethylhexanes was 9.2. The calculated research octane number was 94.2. The results are shown in Table 2.

Example 3

7.002 g (0.0139 mol) of tributylphosphonium heptachlorodialuminate ionic liquid from example 1A was loaded in a 300 cc autoclave with 0.304 g (0.0033 mol) of 2-chlorobutane. Here, less 2-chlorobutane was used compared to example 2. The autoclave was fitted with a Cowles-type impeller. 80 g of isobutane was charged and the reactor was pressurized to about 3.4 MPa(g) (500 psig) with nitrogen. After pressurizing the reactor, the mixture was stirred at 1700-1900 rpm for 20 minutes to ensure breakdown of the 2-chlorobutane. The reaction was initiated by the addition of approximately 8 g of 2-butenes (mixed cis- and trans-isomers) over the course of 2.5 minutes while mixing at 1900 rpm. The 2-butenes blend also contained about 8.5 wt % n-pentane that was used as a tracer to verify the amount of butenes added. The mixing was stopped, and the mixture was allowed to settle. The hydrocarbon was analyzed by gas chromatography (GC). Table 2 shows the results. The n-pentane tracer indicated that 7.30 g of 2-butenes were added. The butenes conversion was 99.94%. The hydrocarbon contained 18.4 wt % $C_{5+}$. Of the $C_{5+}$ products, 76% was octanes, 6.7% was isopentane, 4.9% was hexanes, 4.5% was heptanes and 7.9% was $C_{9+}$. Among the octanes, the ratio of trimethylpentanes to dimethylhexanes was 11.0. The calculated research octane number was 95.2. The results are shown in Table 2.

Example 4

7.204 g (0.0125 mol) of tributylpentylphosphonium heptachlorodialuminate ionic liquid and 0.814 g (0.0016 mol) tributylphosphonium heptachlorodialuminate ionic liquid from example 1A were both loaded in a 300 cc autoclave with 0.425 g (0.0046 mol) of 2-chlorobutane. The autoclave was fitted with a Cowles-type impeller. 80 g of isobutane was charged and the reactor was pressurized to about 3.4 MPa(g) (500 psig) with nitrogen. After pressurizing the reactor, the mixture was stirred at 1700-1900 rpm for 20 minutes to ensure breakdown of the 2-chlorobutane. The reaction was initiated by the addition of approximately 8 g of 2-butenes (mixed cis- and trans-isomers), over the course of 2.5 minutes while mixing at 1900 rpm. The 2-butenes blend also contained about 8.5 wt % n-pentane that was used as a tracer to verify the amount of butenes added. The mixing was stopped, and the mixture was allowed to settle. The hydrocarbon was analyzed by gas chromatography (GC). Table 2 shows the results. The n-pentane tracer indicated that 8.12 g of 2-butenes were added. The butenes conversion was 99.96%. The hydrocarbon contained 19.8 wt % $C_{5+}$. Of the $C_{5+}$ products, 74.0% was octanes, 6.6% was isopentane, 5.6% was hexanes, 4.7% was heptanes and 9.0% was $C_{9+}$ (products containing 9 carbon atoms or more). Among the octanes, the ratio of trimethylpentanes to dimethylhexanes was 13.3. The calculated research octane number was 95.5. The results are shown in Table 2.

TABLE 2

Alkylation Reactions with Tributylphosphonium-$Al_2Cl_7$ and Comparison to Tributylpentylphosphonium-$Al_2Cl_7$

|  | Comp 1 | Ex 2 | Ex 3 | Ex 4 |
|---|---|---|---|---|
| IL cation | TBPP | TBP | TBP | 88.7 mol % TBPP, 11.3 mol % TBP |
| 2-chlorobutane added (g) | 0.422 | 0.335 | 0.304 | 0.425 |
| Butenes conversion | 99.94% | 99.95% | 99.94% | 99.96% |
| wt % $C_{5+}$ | 19.5% | 19.6% | 18.4% | 19.8% |
| $C_5$ wt % sel. | 6.8% | 5.7% | 6.7% | 6.6% |
| $C_6$ wt % sel. | 5.8% | 4.6% | 4.9% | 5.6% |
| $C_7$ wt % sel. | 5.1% | 8.7% | 4.5% | 4.7% |
| $C_8$ wt % sel. | 72.3% | 72.4% | 76.0% | 74.0% |
| $C_{9+}$ wt % sel. | 10.1% | 8.7% | 7.9% | 9.0% |
| TMP/DMH | 12.6 | 9.2 | 11.0 | 13.3 |
| RONC | 95.1 | 94.2 | 95.2 | 95.5 |

Example 5

The kinematic viscosity of TBP-$Al_2Cl_7$ ionic liquid prepared in example 1A was measured. It had kinematic viscosity of 31.50 cSt at 25° C., 19.86 cSt at 38° C. and 13.91 cSt at 50° C. That is more viscous than 1-butyl-3-methyl imidazolium-$Al_2Cl_7$ (BMIM-$Al_2Cl_7$) (about 13 to 15 cSt at 25° C.), but lower than tribtuylmethylphosphonium-$Al_2Cl_7$ (TBMP-$Al_2Cl_7$) (about 55 to 57 cSt at 25° C.) or tributylpentylphosphonium-$Al_2Cl_7$ (TBPP-$Al_2Cl_7$) (about 80-95 cSt at 25° C.). Table 3 gives the kinematic viscosity for TBP-$Al_2Cl_7$, TBPP-$Al_2Cl_7$, and a blend of 10 wt % TBP-$Al_2Cl_7$ and 90 wt % TBPP-$Al_2Cl_7$.

The relative density of the ionic liquid was also measured at 25° C. using ASTM method D4052. The relative density was 1.2203 $g/cm^3$.

TABLE 3

Kinematic viscosity

| IL | Al/P mol | Kinematic viscosity at 25° C. (cSt) | Kinematic viscosity at 38° C. (cSt) | Kinematic viscosity at 50° C. (cSt) |
|---|---|---|---|---|
| TBP | 2.07 | 31.50 | 19.86 | 13.91 |
| TBPP | 2.16 | 83.81 | 48.39 | 31.51 |
| TBPP | 1.95 | 90.49 | 52.12 | 34.20 |
| 10 wt % TBP, 90 wt % TBPP | 10 wt % $Bu_3PH$ (2.07 Al/P), 90 wt % TBPP (1.95 Al/P) | 78.19 | 45.91 | 30.18 |

Example 6

The melting point of TBP-Al$_2$Cl$_7$ prepared in example 1A was measured. Melting occurred between 15-17° C.

Example 7

The spent ionic liquid from example 2 was analyzed by NMR (in CDCl$_3$) to determine if alkylation of the phosphonium occurred. The main resonance known to be tri(n-butyl) phosphonium heptachlorodialuminate was observed in the $^{31}$P NMR at 13.5 ppm. A second resonance corresponding to 4 mol % occurred at 21.8 ppm, corresponding to di(n-butyl)(s-butyl)phosphonium. However, it is not the expected alkylation product of tributylphosphonium and butene (tetra-butylphosphonium), which would have had a peak at 34 ppm (tetra n-butylphosphonium). The alkylate was also analyzed by $^{31}$P NMR to check for extraction of the phosphonium into the hydrocarbon phase. No resonances were observed. Elemental analysis by inductively charged plasma atomic emission spectroscopy of the alkylate product shows that no detectable phosphorous was found.

By the term "about," we mean within 10% of the value, or within 5%, or within 1%.

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention. It being understood that various changes may be made in the function and arrangement of elements described in an exemplary embodiment without departing from the scope of the invention as set forth in the appended claims.

SPECIFIC EMBODIMENTS

While the following is described in conjunction with specific embodiments, it will be understood that this description is intended to illustrate and not limit the scope of the preceding description and the appended claims.

A first embodiment of the invention is a process comprising contacting an isoparaffin feed having from 4 to 10 carbon atoms and an olefin feed having from 2 to 10 carbon atoms in the presence of a trialkylphosphonium ionic liquid catalyst composition in an alkylation zone under alkylation conditions to generate an alkylate, wherein the trialkylphosphonium ionic liquid catalyst composition comprises one or more trialkylphosphonium haloaluminate compounds having a formula:

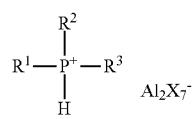

where R$^1$, R$^2$, and R$^3$ are the same or different and each is independently selected from C$_1$ to C$_8$ hydrocarbyl; and X is selected from F, Cl, Br, I, or combinations thereof. An embodiment of the invention is one, any or all of prior embodiments in this paragraph up through the first embodiment in this paragraph wherein R$^1$, R$^2$, and R$^3$ are C$_1$ to C$_6$ hydrocarbyl. An embodiment of the invention is one, any or all of prior embodiments in this paragraph up through the first embodiment in this paragraph wherein R$^1$, R$^2$, and R$^3$ have the same number of carbon atoms. An embodiment of the invention is one, any or all of prior embodiments in this paragraph up through the first embodiment in this paragraph wherein R$^1$, R$^2$, and R$^3$ are identical. An embodiment of the invention is one, any or all of prior embodiments in this paragraph up through the first embodiment in this paragraph wherein each of R$^1$, R$^2$, and R$^3$ is selected from the group consisting of methyl, ethyl, propyl, butyl, pentyl, and hexyl. An embodiment of the invention is one, any or all of prior embodiments in this paragraph up through the first embodiment in this paragraph wherein the trialkylphosphonium haloaluminate compound comprises tri-n-butylphosphonium Al$_2$Cl$_7$—, tri-isobutylphosphonium Al$_2$Cl$_7$—, or di-n-butyl-sec-butylphosphonium Al$_2$Cl$_7$—. An embodiment of the invention is one, any or all of prior embodiments in this paragraph up through the first embodiment in this paragraph wherein an initial kinematic viscosity of the trialkylphosphonium ionic liquid catalyst composition is less than about 70 cSt at 25° C. An embodiment of the invention is one, any or all of prior embodiments in this paragraph up through the first embodiment in this paragraph wherein a molar ratio of aluminum to phosphorous in the ionic liquid catalyst composition is in the range of 1.8 to 2.2. An embodiment of the invention is one, any or all of prior embodiments in this paragraph up through the first embodiment in this paragraph wherein the trialkylphosphonium ionic liquid catalyst composition further comprises a quaternary phosphonium haloaluminate compound having a formula:

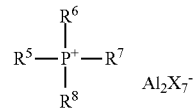

where R$^5$-R$^7$ are the same or different and each is independently selected from a C$_1$ to C$_8$ hydrocarbyl; R$^8$ is different from R$^5$-R$^7$ and is selected from a C$_1$ to C$_{15}$ hydrocarbyl; and X is selected from F, Cl, Br, I, or combinations thereof. An embodiment of the invention is one, any or all of prior embodiments in this paragraph up through the first embodiment in this paragraph wherein the trialkylphosphonium ionic liquid catalyst composition further comprises a co-catalyst. An embodiment of the invention is one, any or all of prior embodiments in this paragraph up through the first embodiment in this paragraph wherein the co-catalyst comprises a Brønsted acid selected from the group consisting of HCl, HBr, HI, and mixtures thereof, or a Brønsted acid precursor. An embodiment of the invention is one, any or all of prior embodiments in this paragraph up through the first embodiment in this paragraph further comprising separating the alkylate and unreacted isoparaffin feed from the trialkylphosphonium ionic liquid catalyst composition to form a hydrocarbon stream comprising the alkylate and the unreacted isoparaffin feed and an ionic liquid stream comprising the trialkylphosphonium ionic liquid catalyst composition; separating the hydrocarbon stream into an alkylate stream and an unreacted isoparaffin stream; and recycling at least one of the unreacted isoparaffin stream and the ionic liquid stream. An embodiment of the invention is one, any or all of prior embodiments in this paragraph up through the first embodiment in this paragraph further comprising regenerating at least a portion of the trialkylphosphonium ionic liquid catalyst composition in the ionic liquid stream; and recycling the regenerated trialkylphosphonium ionic liquid catalyst to the alkylation zone. An embodiment of the invention is one, any or all of prior embodiments in this paragraph up through the first embodiment in this paragraph wherein the trialkylphosphonium ionic liquid catalyst is present in an amount of about 1 vol % to about 75 vol % of a total volume of material in the alkylation zone. An embodiment of the invention is one, any or all of prior embodiments in this paragraph up through the first embodiment in this paragraph wherein the alkylation conditions include a temperature of from about 0° C. to about 100° C., a pressure from about 0.3 MPa(g) to about 2.5 MPa(g), an overall paraffin to olefin molar ratio from about 2 to about 20, and a residence time of about 1 min to about 1 hour. An embodiment of the invention is one, any or all of prior embodiments in this paragraph up through the first embodiment in this paragraph wherein the isoparaffin feed has from 4 to 8 carbon atoms and the olefin feed has from 3 to 8 carbon atoms. An embodiment of the invention is one, any or all of prior embodiments in this paragraph up through the first embodiment in this paragraph wherein the isoparaffin has from 4 to 5 carbon atoms and the olefin has from 3 to 5 carbon atoms.

A second embodiment of the invention is a process comprising contacting an isoparaffin feed having from 4 to 6 carbon atoms and an olefin feed having from 2 to 6 carbon atoms in the presence of a trialkylphosphonium ionic liquid catalyst composition in an alkylation zone under alkylation conditions to generate an alkylate, wherein the trialkylphosphonium ionic liquid catalyst composition comprises one or more trialkylphosphonium haloaluminate compounds and a co-catalyst, the trialkylphosphonium haloaluminate compound having a formula:

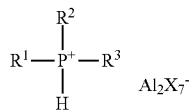

where $R^1$, $R^2$, and $R^3$ are the same or different and each is independently selected from $C_1$ to $C_8$ hydrocarbyl; X is selected from F, Cl, Br, I, or combinations thereof; wherein the co-catalyst comprises a Brønsted acid selected from the group consisting of HCl, HBr, HI, and mixtures thereof, or a Brønsted acid precursor, and wherein the alkylation conditions include a temperature of from about 0° C. to about 100° C., a pressure from about 0.3 MPa(g) to about 2.5 MPa(g), a paraffin to olefin molar ratio from about 2 to about 20, and a residence time of about 1 min to about 1 hour. An embodiment of the invention is one, any or all of prior embodiments in this paragraph up through the second embodiment in this paragraph further comprising separating the alkylate and unreacted isoparaffin feed from the trialkylphosphonium ionic liquid catalyst to form a hydrocarbon stream comprising the alkylate and the unreacted isoparaffin feed and an ionic liquid stream comprising the trialkylphosphonium ionic liquid catalyst; separating the hydrocarbon stream into an alkylate stream and an unreacted isoparaffin stream; and recycling at least one of the unreacted isoparaffin stream and the ionic liquid stream. An embodiment of the invention is one, any or all of prior embodiments in this paragraph up through the second embodiment in this paragraph wherein the trialkylphosphonium ionic liquid catalyst composition further comprises a quaternary phosphonium haloaluminate compound having a formula:

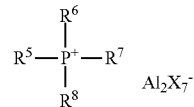

where $R^5$-$R^7$ are the same or different and each is independently selected from a $C_1$ to $C_8$ hydrocarbyl; $R^8$ is different from $R^5$-$R^7$ is selected from a $C_1$ to $C_{15}$ hydrocarbyl; and X is selected from F, Cl, Br, I, or combinations thereof.

Without further elaboration, it is believed that using the preceding description that one skilled in the art can utilize the present invention to its fullest extent and easily ascertain the essential characteristics of this invention, without departing from the spirit and scope thereof, to make various changes and modifications of the invention and to adapt it to various usages and conditions. The preceding preferred specific embodiments are, therefore, to be construed as merely illustrative, and not limiting the remainder of the disclosure in any way whatsoever, and that it is intended to cover various modifications and equivalent arrangements included within the scope of the appended claims.

In the foregoing, all temperatures are set forth in degrees Celsius and, all parts and percentages are by weight, unless otherwise indicated.

What is claimed:

1. An alkylation process comprising:
   contacting an isoparaffin feed having from 4 to 10 carbon atoms and an olefin feed having from 2 to 10 carbon atoms in the presence of a trialkylphosphonium ionic liquid catalyst composition in an alkylation zone under alkylation conditions to generate an alkylate,
   wherein the trialkylphosphonium ionic liquid catalyst composition comprises one or more trialkylphosphonium haloaluminate compounds having a formula:

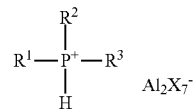

where $R^1$, $R^2$, and $R^3$ are the same or different and each is independently selected from $C_1$ to $C_8$ hydrocarbyl; and
   X is selected from F, Cl, Br, I, or combinations thereof;
   wherein the trialkylphosphonium haloaluminate compound comprises tri-n-butylphosphonium $Al_2Cl_7$, tri-isobutylphosphonium $Al_2Cl_7$, or di-n-butyl-sec-butylphosphonium $Al_2Cl_7$; and
   wherein an initial kinematic viscosity of the trialkylphosphonium ionic liquid catalyst composition is less than 50 cSt at 25° C.

2. The process of claim 1 wherein an initial kinematic viscosity of the trialkylphosphonium ionic liquid catalyst composition is about 30 cSt or less at 25° C.

3. The process of claim 1 wherein a molar ratio of aluminum to phosphorous in the ionic liquid catalyst composition is in the range of 1.8 to 2.2.

4. The process of claim 1 wherein the trialkylphosphonium ionic liquid catalyst composition further comprises a quaternary phosphonium haloaluminate compound having a formula:

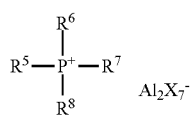

where $R^5$-$R^7$ are the same or different and each is independently selected from a $C_1$ to $C_8$ hydrocarbyl;

$R^8$ is different from $R^5$-$R^7$ and is selected from a $C_1$ to $C_{15}$ hydrocarbyl; and X is selected from F, Cl, Br, I, or combinations thereof.

5. The process of claim 1 wherein the trialkylphosphonium ionic liquid catalyst composition further comprises a co-catalyst.

6. The process of claim 5 wherein the co-catalyst comprises a Brønsted acid selected from the group consisting of HCl, HBr, HI, and mixtures thereof, or a Brønsted acid precursor.

7. The process of claim 1 further comprising:
separating the alkylate and unreacted isoparaffin feed from the trialkylphosphonium ionic liquid catalyst composition to form a hydrocarbon stream comprising the alkylate and the unreacted isoparaffin feed and an ionic liquid stream comprising the trialkylphosphonium ionic liquid catalyst composition;
separating the hydrocarbon stream into an alkylate stream and an unreacted isoparaffin stream; and
recycling at least one of the unreacted isoparaffin stream and the ionic liquid stream.

8. The process of claim 1 further comprising:
regenerating at least a portion of the trialkylphosphonium ionic liquid catalyst composition in the ionic liquid stream; and
recycling the regenerated trialkylphosphonium ionic liquid catalyst to the alkylation zone.

9. The process of claim 1 wherein the trialkylphosphonium ionic liquid catalyst is present in an amount of about 1 vol % to about 75 vol % of a total volume of material in the alkylation zone.

10. The process of claim 1 wherein the alkylation conditions include a temperature of from about 0° C. to about 100° C., a pressure from about 0.3 MPa(g) to about 2.5 MPa(g), an overall paraffin to olefin molar ratio from about 2 to about 20, and a residence time of about 1 min to about 1 hour.

11. The process of claim 1 wherein the isoparaffin feed has from 4 to 8 carbon atoms and the olefin feed has from 3 to 8 carbon atoms.

12. The process of claim 11 wherein the isoparaffin has from 4 to 5 carbon atoms and the olefin has from 3 to 5 carbon atoms.

* * * * *